United States Patent
Kim et al.

(10) Patent No.: US 11,491,664 B2
(45) Date of Patent: Nov. 8, 2022

(54) ROBOTIC PLATFORM MANIPULATING PERIPEHERAL NERVE SYSTEM

(71) Applicants: KOREA INSTITUTE OF SCIENCE AND TECHNOLOGY, Seoul (KR); RESEARCH & BUSINESS FOUNDATION SUNGKYUNKWAN UNIVERSITY, Suwon-si (KR)

(72) Inventors: Keehoon Kim, Seoul (KR); Yong Seok Ihn, Seoul (KR); Donghyun Hwang, Seoul (KR); Sehyuk Yim, Seoul (KR); Sang Rok Oh, Seoul (KR); Jinwoo Jeong, Seoul (KR)

(73) Assignees: Korea Institute of Science and Technology, Seoul (KR); Research & Business Foundation Sungkyunkwan University, Suwon-si (KR)

( * ) Notice: Subject to any disclaimer, the term of this patent is extended or adjusted under 35 U.S.C. 154(b) by 628 days.

(21) Appl. No.: 16/566,795

(22) Filed: Sep. 10, 2019

(65) Prior Publication Data

US 2021/0069914 A1 Mar. 11, 2021

(51) Int. Cl.
*B25J 9/00* (2006.01)
*B25J 15/00* (2006.01)

(52) U.S. Cl.
CPC ......... *B25J 15/0057* (2013.01); *B25J 9/0009* (2013.01); *B25J 9/0084* (2013.01)

(58) Field of Classification Search
CPC .... B25J 9/0084; B25J 9/0009; B25J 15/0057; A61B 34/30; A61B 2034/305
See application file for complete search history.

(56) References Cited

U.S. PATENT DOCUMENTS 11,241,330 B1 * 2/2022 Sabir ...................... B02C 18/10
11,338,527 B2 * 5/2022 Dunlap ................ B29C 65/228

FOREIGN PATENT DOCUMENTS

| KR | 10-2011-0030038 A | 3/2011 |
| KR | 10-1161242 B1 | 7/2012 |
| KR | 10-2015-0022414 A | 3/2015 |

OTHER PUBLICATIONS

Chen et al., A design of surgical robotic system based on 6-DOF parallel mechanism, 2018, IEEE, p. 10-14 (Year: 2018).*
Lozano-Perez, Robot programming, 1983, IEEE, p. 821-841 (Year: 1983).*
Wang et al., A Novel Master Manipulator with Force Feedback for Robot-Assisted Natural Orifice Transluminal Endoscopic Surgery, 2019, IEEE, pg. (Year: 2019).*
Yuan et al., Design and prototyping a cable-driven multi-stage telescopic arm for mobile surveillance robots, 2014, IEEE, p. 1845-1850 (Year: 1850).*

* cited by examiner

*Primary Examiner* — McDieunel Marc
(74) *Attorney, Agent, or Firm* — Rabin & Berdo, P.C.

(57) ABSTRACT

A robotic platform manipulating peripheral nerve system includes a manipulator and a recorder. The manipulator includes a rotating guide, a plurality of rotating movers and a plurality of manipulating units. The rotating guide has an opening portion through which the recorder records, and has a guide rail at a side. The rotating movers are combined with the rotating guide and move along the guide rail. The manipulating units are respectively fixed to the rotating movers, and a manipulating part performs the operation being connected to an end of each of the manipulating units.

17 Claims, 11 Drawing Sheets

ROBOTIC PLATFORM MANIPULATING PERIPEHERAL NERVE SYSTEM

BACKGROUND

1. Field of Disclosure

The present disclosure of invention relates to a robotic platform, and more specifically the present disclosure of invention relates to a robotic platform manipulating peripheral nerve system performing an operation on a fine nerve interface, such as peripheral nerve manipulation of neural prosthetic using a peripheral nerve signal.

2. Description of Related Technology

Recently, a neural prosthetic like an orthosis, an artificial arm or an artificial leg, using a peripheral nerve signal, has been developed, and a key technology in the peripheral nerve signal based neural prosthetic is a stable transplant of a nerve interface device recording and stimulating a nerve signal.

However, the peripheral nerve is enclosed by epineurium which is very flexible but durable and slippery, and thus the peripheral nerve is hard to be controlled. In addition, an excessive control of the peripheral nerve for inserting the nerve interface may cause a damage to the nerve, and thus the transplant of the nerve interface device is very difficult.

Thus, until now, a skilled surgery performs the transplant using a fine operation method, and individual appliers are often used for the operation but are very limited in the operation.

Further, the device developed for the nerve interface device may have very complex shape and thus, the operation time may be increased more and the damage to the nerve may occur more often. Thus, for the stable transplant of the nerve interface device, the robot system used in an entire operating process and a platform having a function of instant measuring the nerve signal and stimulating of the nerve, are necessary.

Related prior art is Korean patent No. 10-1161242.

SUMMARY

The present invention is developed to solve the above-mentioned problems of the related arts. The present invention provides a robotic platform having a relatively simple structure and performing a transplant of a nerve interface more finely, precisely and stably, to minimize a possibility of the damage of the nerve.

According to an example embodiment, a robot platform includes a manipulator and a recorder. The manipulator performs an operation over an operating table. The recorder records the operation through the manipulator. The manipulator includes a rotating guide, a plurality of rotating movers and a plurality of manipulating units. The rotating guide has an opening portion through which the recorder records, and has a guide rail at a side. The rotating movers are combined with the rotating guide and move along the guide rail. The manipulating units are respectively fixed to the rotating movers, and a manipulating part performs the operation being connected to an end of each of the manipulating units.

In an example, the rotating guide may have a circular plate shape, and the rotating movers may rotate with respect to a center of the rotating guide along the guide rail.

In an example, each of the rotating movers may include an upper block, a lower block and a central block. The upper block may be disposed at an upper side of the rotating guide and partially face an upper side of the rotating guide. The lower block may be disposed at a lower side of the rotating guide and partially face a lower side of the rotating guide. The central block may connect the upper block with the lower block, and move along the guide rail. The manipulating unit may be fixed to a rear side of the central block.

In an example, each of the manipulating units may further include an upper unit fixed to the rotating mover, and a central unit connected to the upper unit. The manipulating unit may be connected to a lower side of the central unit. Each of the upper unit and the central unit may have three degrees of freedom, capable of moving along a first direction X, a second direction Y and a third direction Z substantially perpendicular to one another.

In an example, the upper unit may include an upper connecting block fixed to the rotating mover, an upper moving block moving along the third direction with respect to the upper connecting block at a rear side of the upper connecting block, and a connecting frame connecting the upper moving block with the central unit.

In an example, the upper unit may be disposed at an outside of the rotating guide, and the connecting frame may extend from the outside of the rotating guide to a lower portion of the rotating guide along an inclined direction so that the central unit and the manipulating unit may be disposed at an inside lower portion of the rotating guide.

In an example, the central unit may include a central connecting block connected to the upper unit and moving along the first direction with the upper unit, a first moving block connected to a lower portion of the central connecting block, and a second moving block moving along the second direction with respect to the first moving block at a lower portion of the first moving block.

In an example, the manipulating part may include a fixing unit rotating with respect to the central unit with a rotating axis of the third direction, a manipulating frame rotating with respect to the fixing unit with an rotating axis of a forth direction U, and a needle unit moving along a fifth direction V with respect to the manipulating frame In an example, the fourth direction may be inclined with respect to the first direction by a first angle, and the fifth direction may be inclined with respect to the first direction by a second angle different from the first angle.

In an example, the fixing unit may include a pair of vertical extending portions extending along the third direction from an extending rotating portion of the central unit, a horizontal extending portion connecting ends of the pair of vertical extending portions with each other, and a pair of circular fixing portions fixed to a center of each of the pair of vertical extending portions. The extending rotating portion may rotate with respect to the third direction. The manipulating frame may pass between the pair of circular fixing portions.

In an example, the manipulating portion may further include a body cover passing through and fixing the fixing unit along the fourth direction. The manipulating frame may include a body portion passing through the body cover, and rotating with respect to the body cover with a rotating axis of the fourth direction, an extending portion extending from the body portion, and a sliding base forming a sliding surface along the fifth direction at an end of the extending portion.

In an example, the needle unit may include a needle base sliding along the fifth direction with respect to the manipulating frame, a needle disposed on the needle base, and a needle fixing portion fixing the needle.

In an example, the manipulating part may include a first rotating part rotating with respect to the central unit with a rotating axis of the third direction, a fixing unit covering the first rotating part and extending along the third direction, a manipulating frame combined with the fixing unit and rotating with respect to the second direction and a sixth direction U', and a needle unit moving along a seventh direction V' with respect to the manipulating frame.

In an example, the sixth direction may be inclined with respect to the first direction by a third angle, and the seventh direction may be inclined with respect to the first direction by a fourth angle different from the third angle.

In an example, the manipulating frame may include a rotating boy combined with an end of the fixing unit and rotating with respect to the second direction, an extending portion extending along the sixth direction from the rotating boy, and a second rotating portion combined with the extending portion and rotating with respect to the sixth direction.

In an example, the manipulating frame may further include a rotating base fixed to an end surface of the second rotating portion, and a sliding base forming a sliding surface from an end of the rotating base to the seventh direction.

In an example, the needle unit may include a needle base sliding along the seventh direction with respect to the manipulating frame, a needle disposed on the needle base, and a needle fixing portion fixing the needle.

According to the present example embodiments, an operation on a fine nerve interface like a peripheral nerve manipulation may be performed more accurately, precisely and finely. The robotic platform may have a relatively simple structure and perform all kinds of driving, and thus the operation may be performed with various kinds of positions and postures.

The robotic platform has many degrees of freedom, and thus fine, accurate, precise and complex operation may be performed, and a plurality of manipulating units may be positioned at various kinds of positions on a rotating guide and thus the operation may be performed more efficiently.

Here, an upper unit and a central unit move in a horizontal direction along first to third directions, and a manipulating part rotates or slides along two axes inclined with respect to the first direction additionally, and thus a needle may perform the operation with various kinds of positions and postures.

In addition, the needle performing the operation accesses to an object with sliding, and thus the operation may be performed more accurately and precisely. Various kinds of needles may be selected, and various kinds of operations may be performed.

In addition, the operation may be recorded and monitored through a central opening portion, and the feed-back control for preventing the position or the posture of the manipulating units from interfering in the operation may be performed.

Figure 1:
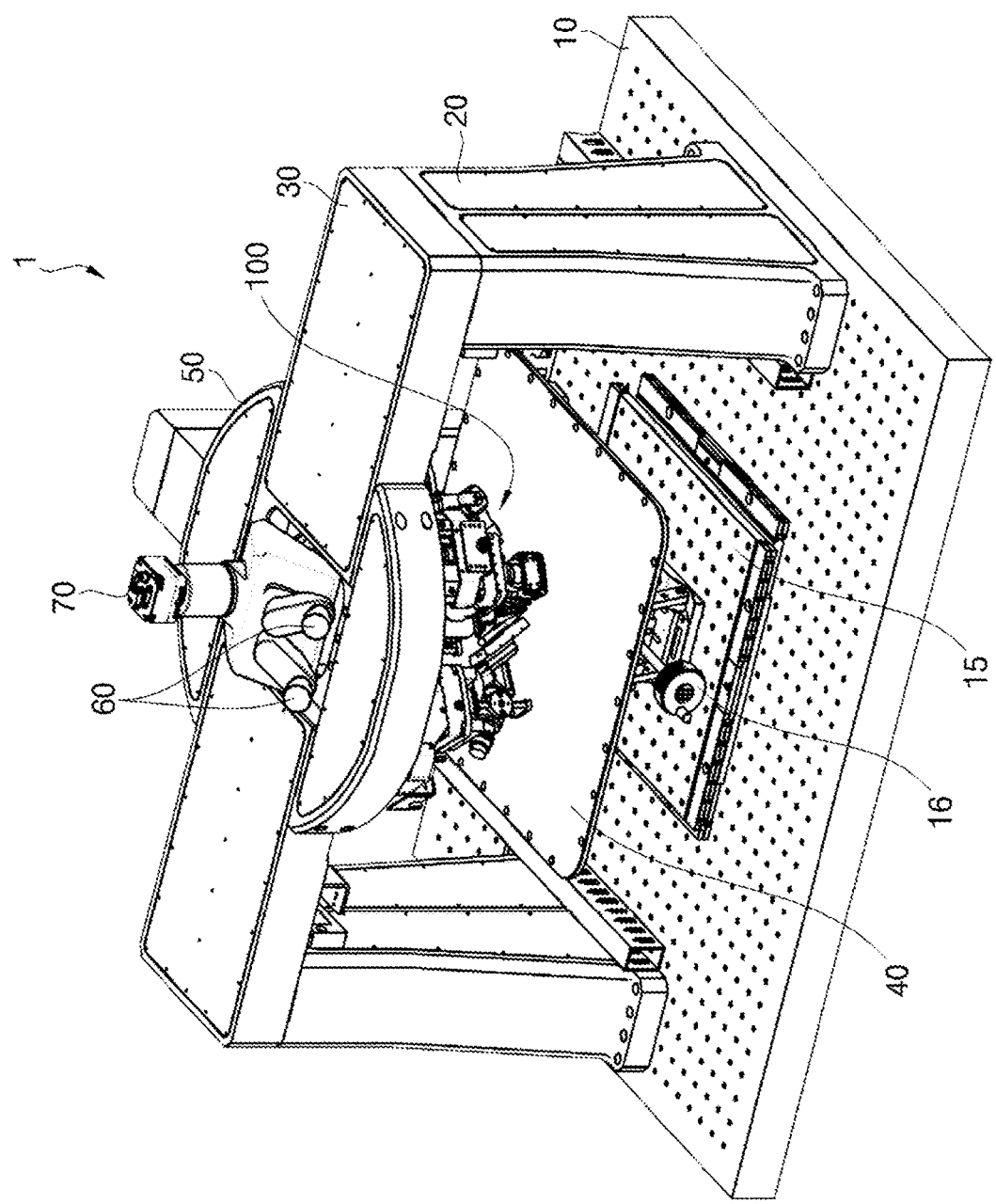
FIG. 1 is a perspective view illustrating a robot platform manipulating a peripheral nerve according to an example embodiment of the present invention.

| * Reference numerals | |
|---|---|
| 1: robot platform | 100: manipulator |
| 110: rotating guide | 120: guide rail |
| 130: rotating mover | 200, 201: manipulating unit |
| 300: upper unit | 310: upper connecting block |
| 320: upper moving block | 330: upper driver |
| 340: upper transmission | 350: upper frame |
| 360: connecting frame | 400: central unit |
| 410: central connecting block | 420: first moving block |
| 430: second moving block | 440: extending block |
| 500, 600: manipulating part | 530, 630: manipulating frame |
| 540: body driver | 550, 650: needle unit |
| 610: first rotating part | |

DETAILED DESCRIPTION

The invention is described more fully hereinafter with Reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention is described more fully hereinafter with reference to the accompanying drawings, in which embodiments of the invention are shown.

FIG. 1 is a perspective view illustrating a robot platform manipulating a peripheral nerve according to an example embodiment of the present invention.

Referring to FIG. 1, the robot platform 1 manipulating a peripheral nerve (hereinafter, robot platform) according to the present example embodiment includes a base frame 10, a vertical frame 20 extending from the base frame 10 vertically, and a horizontal frame 30 extending horizontally between the vertical frames 30.

In addition, the robot platform 1 further includes a circular frame 50 having a circular shape at a center of the horizontal frame 20, and a manipulator 100 positioned at an inside of the circular frame 50 and heading a lower portion.

Further, the robot platform 1 further includes a recorder 70, and a monitor 60. The recorder 70 is fixed at an upper portion of the circular frame 50, and records the operation at an operating position A (FIG. 3) with passing through the manipulator 100. The monitor 60 monitors the operation with passing through the manipulator 100 for an operator to monitor the operation if necessary.

In addition, the robot platform 1 may further include a base 15 disposed on the base frame 10, an operating table 40 on which the operation is performed, and a lifting part 16 lifting up and down the operating table 40.

Thus, in the robot platform 1 according to the present example embodiment, an object which is to be operated, like a peripheral nerve, is positioned on the operating table, and the manipulator 100 is manipulated for the operation.

Here, although not shown in the figure, a manipulating part manipulating the manipulator 100 is connected wirelessly or with wire, for the manipulating, and the operator performs the operation with monitoring the operation using the monitor 60 and the recorder 70.

Hereinafter, the manipulator 100 is explained in detail.

Figure 2:
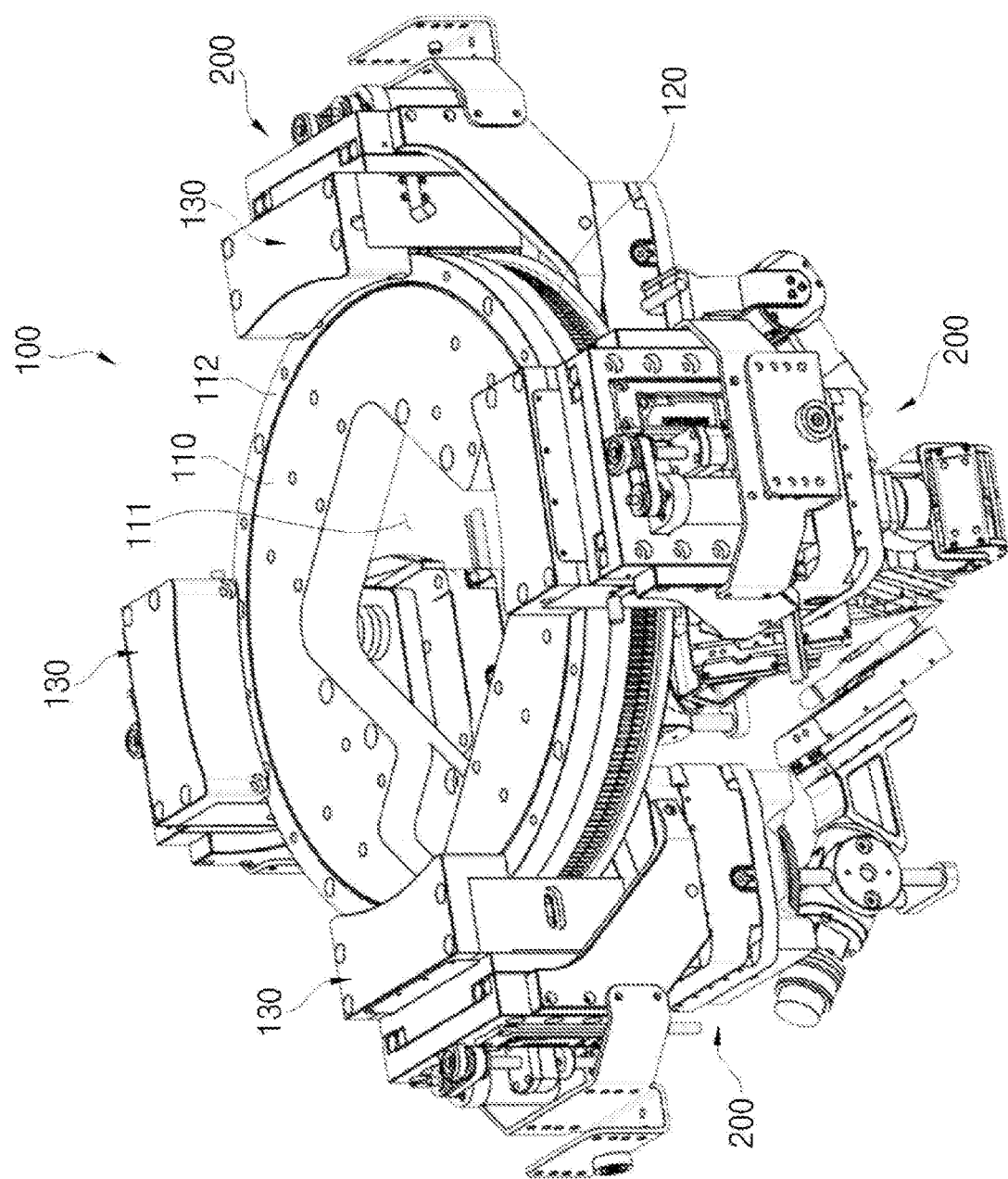
FIG. 2 is a perspective view illustrating a manipulator of the robot platform of FIG. 1.
Figure 3:
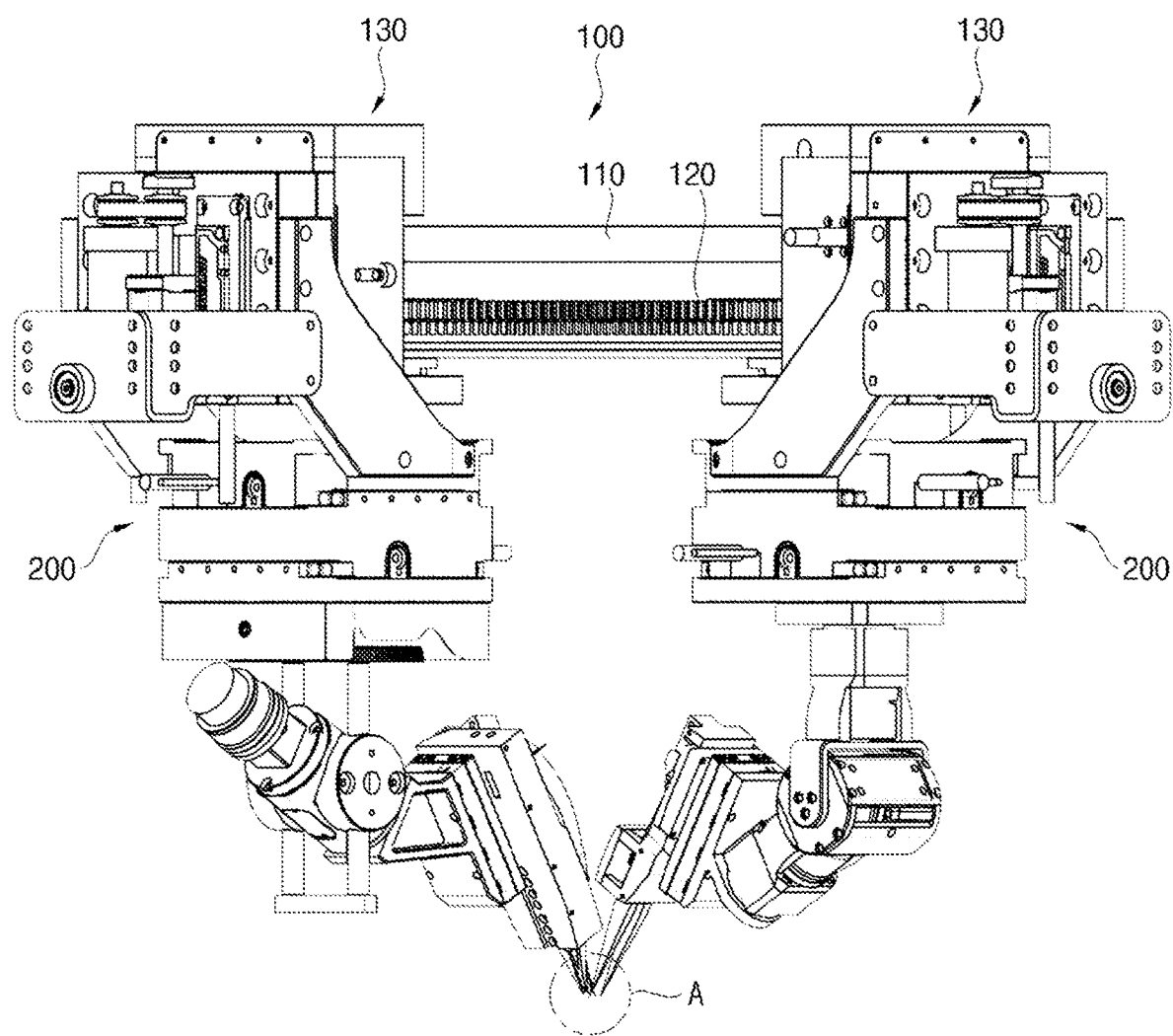
FIG. 3 is a side view illustrating the manipulator of FIG. 2.
Figure 4:
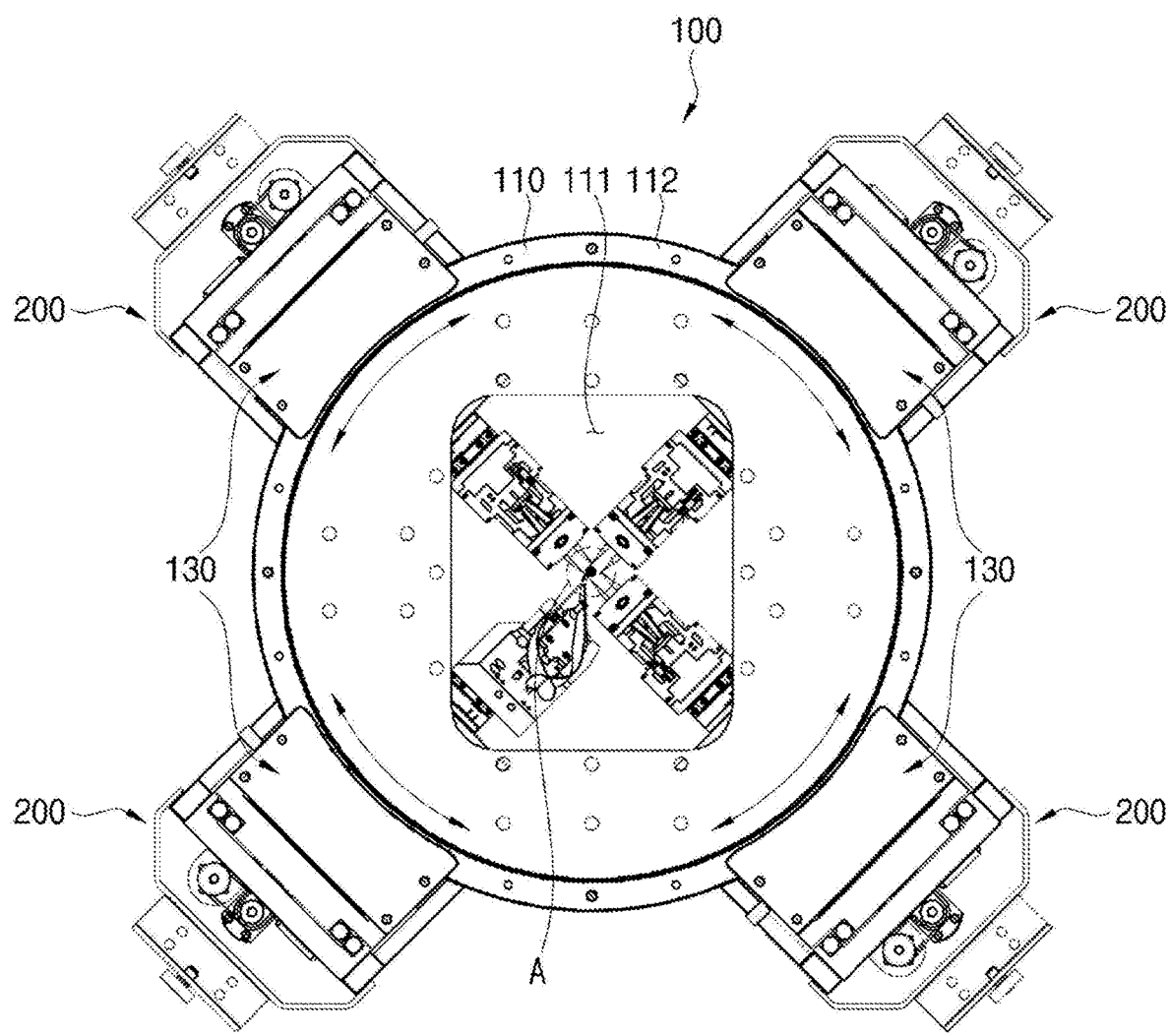
FIG. 4 is a plan view illustrating the manipulator of FIG. 2.
Figure 5:
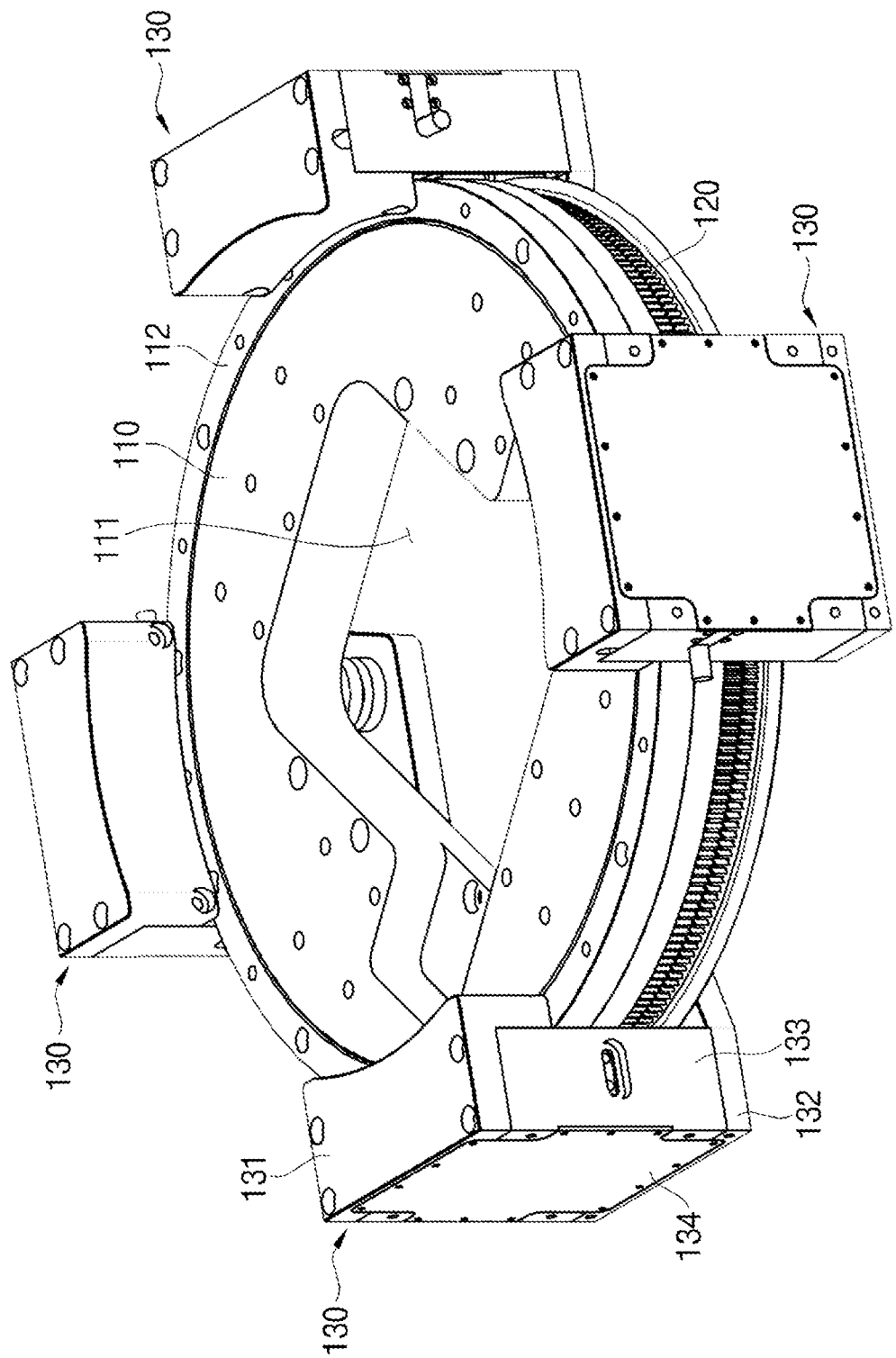
FIG. 5 is a perspective view illustrating a rotating guide and a rotating mover of FIG. 2.

FIG. 2 is a perspective view illustrating a manipulator of the robot platform of FIG. 1. FIG. 3 is a side view illustrating the manipulator of FIG. 2. FIG. 4 is a plan view illustrating the manipulator of FIG. 2. FIG. 5 is a perspective view illustrating a rotating guide and a rotating mover of FIG. 2.

Referring to FIGS. 2 to 5, an upper portion of the manipulator 100 is disposed in the circular frame 50, and a lower portion thereof is protrude to a lower portion of the circular frame 50, for the operation.

Here, the manipulator 100 includes a rotating guide 110, a plurality of rotating movers 130, and a plurality of manipulating units 200.

The rotating guide 110 has a circular plate shape with a predetermined thickness, and has an opening portion 111 at a center. Thus, the recorder 70 passes through the opening portion 111 for recording the operation at the operation position A, and the monitor 60 monitors the operation at the operation position A.

A guide rail 120 is formed at a side of the rotating guide 110, and the rotating movers 130 are positioned at the guide rail 120 and moves at a circumference of the rotating guide 110 along the guide rail 120.

In addition, a rotating slider 112 is formed at upper and lower sides of the rotating guide 110, and thus the rotating movers 130 slide along the rotating slider 112.

The rotating movers 130 moves at the circumference of the rotating guide 110 along the guide rail 120, and thus the rotating movers 130 rotates with respect to the rotating guide 110.

Here, in the figure, four rotating movers are illustrated, but not limited thereto.

Each of the rotating movers 130 has same structure and shape except for the position at the rotating guide 110.

The rotating mover 130 includes an upper block 131, a lower block 132 and a central block 133.

The upper block 131 slides along the rotating slider 112, and a lower portion of the upper block 131 partially overlaps with the rotating slider 112 which is formed at an upper side of the rotating guide 110.

The lower block 132 slides along the rotating slider 112, and an upper portion of the lower block 132 partially overlaps with the rotating slider 112 which is formed at a lower side of the rotating guide 110.

The central block 133 is connected between the upper block 131 and the lower block 132, an inner side of the central block 133 makes contact with the guide rail 120, and the central block 133 moves along the guide rail 120. Here, although not shown in the figure, the central block 133 may moves along the guide rail 120 with an accurate and precise position control.

An outer surface of the central block 133, a rear central surface 134, is fixed with the manipulating unit 200. Thus, when the rotating mover 130 moves along the guide rail 120, the manipulating unit 200 moves along the guide rail 120 with the rotating mover 130.

Hereinafter, the manipulating unit 200 is explained in detail.

Figure 6:
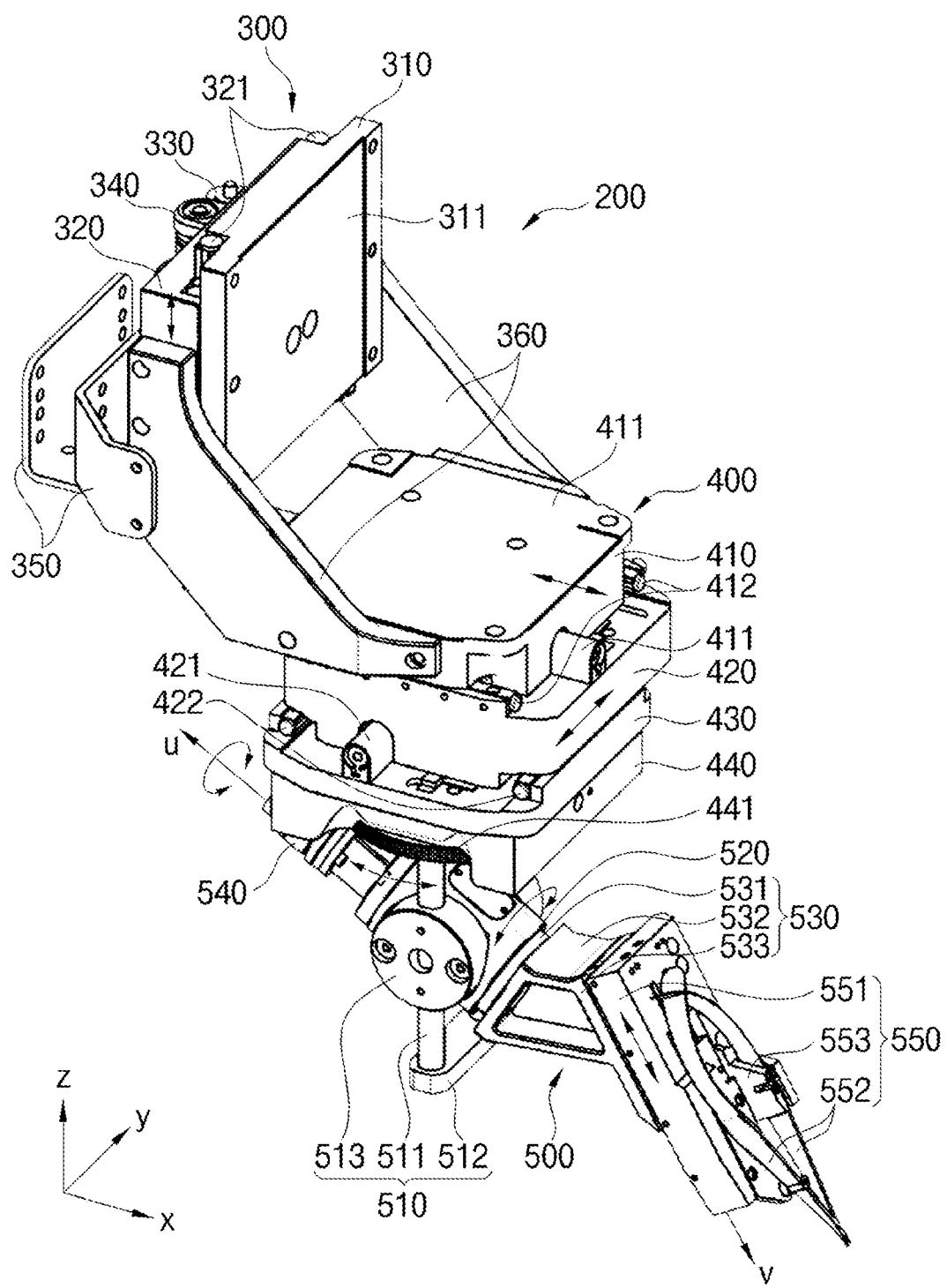
FIG. 6 is a perspective view illustrating a single manipulating unit of the manipulator of FIG. 2.
Figure 7:
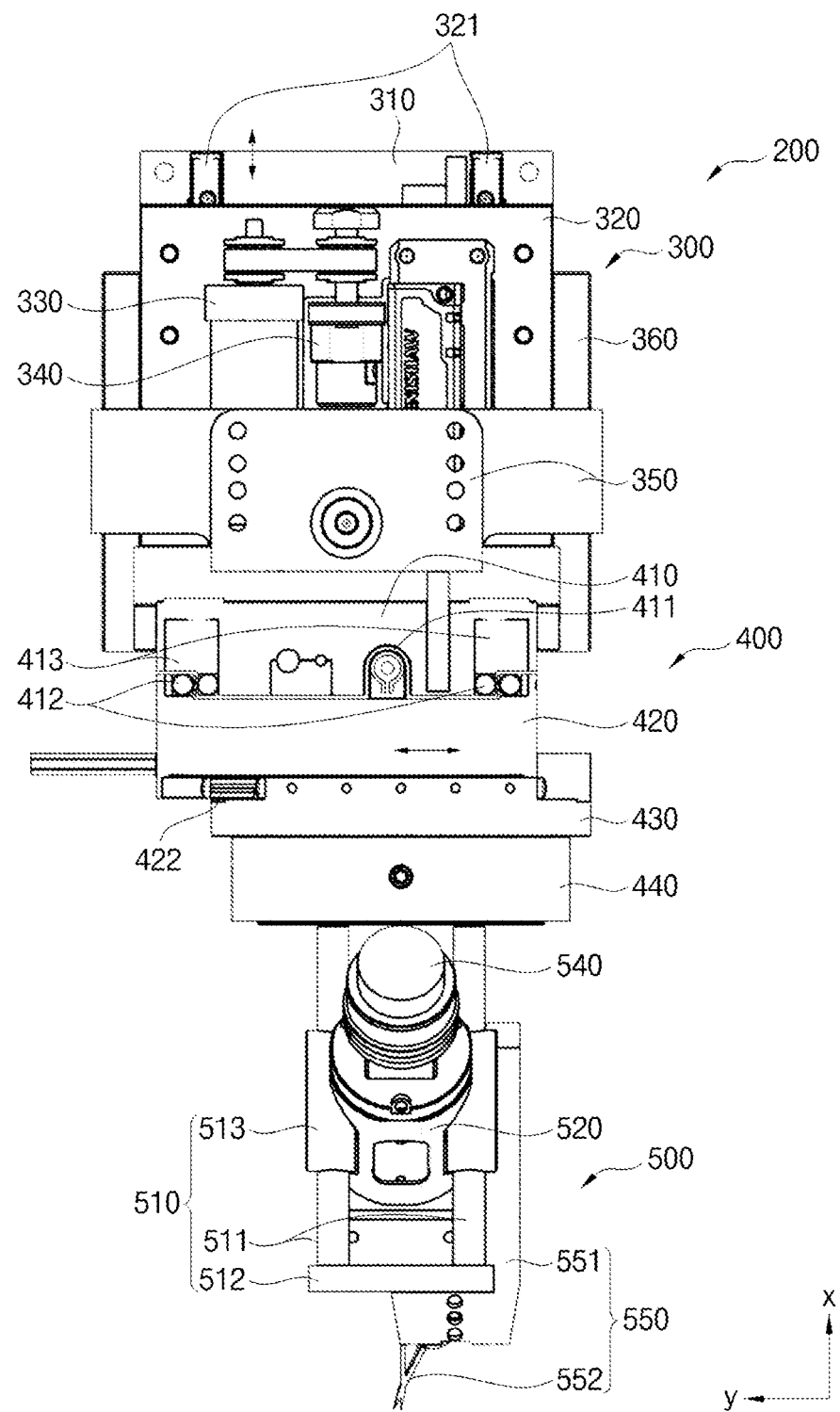
FIG. 7 is a rear view illustrating the manipulating unit of FIG. 6.
Figure 8:
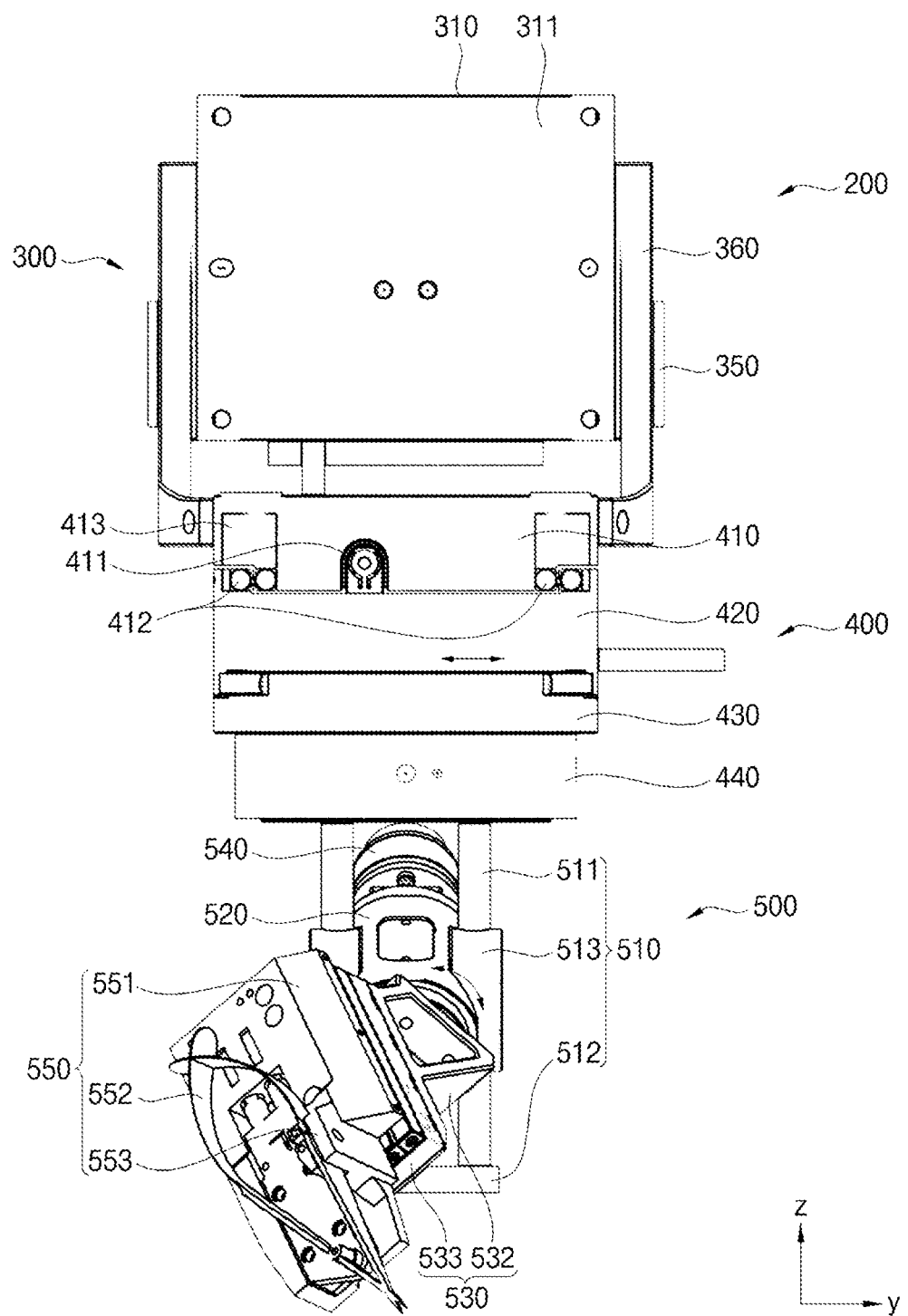
FIG. 8 is a front view illustrating the manipulating unit of FIG. 6.

FIG. 6 is a perspective view illustrating a single manipulating unit of the manipulator of FIG. 2. FIG. 7 is a rear view illustrating the manipulating unit of FIG. 6. FIG. 8 is a front view illustrating the manipulating unit of FIG. 6.

Referring to FIGS. 6 to 8, the manipulating unit 200 includes an upper unit 300, a central unit 400 and a manipulating part 500.

The upper unit 300 is fixed to the rotating mover 130. A needle is fixed to an end of the manipulating part 500 and is to perform the operation. The central unit 400 connects the upper unit 300 with the manipulating part 500.

In the present example embodiment, the upper unit 300 is disposed at an outside of the rotating guide 110, but the manipulating part 500 at which the needle is fixed is disposed at a lower inside of the rotating guide 110, the operating position A, which is a central portion of the rotating guide 110.

As illustrated in FIG. 6, the manipulating part 200 extends from the outside of the rotating guide 110 toward a center of the rotating guide 110 along an inclined direction, and thus, when the operating position A is monitored or recorded through the opening portion 111, elements of the manipulating unit 200 are prevented from being interfered with an viewing angle.

The upper unit 300 includes an upper connecting block 310, an upper moving block 320, an upper driver 330, an upper transmission 340 and an upper frame 350.

The upper connecting block 310 has a rectangular plate shape or a rectangular shape, with extending along a third direction Z. An upper connecting surface 311 which is an inner surface of the upper connecting block 310 has a rectangular shape surface, and is fixed to a central rear surface 134 of the rotating mover 130.

The upper connecting surface 311 and the central rear surface 134 are combined with each other, with substantially corresponding shape.

The upper moving block 320 has a rectangular block shape, makes surface contact with the upper connecting surface 311, and moves along the third direction with respect to the upper connecting surface 311.

Here, an upper guide 321 is disposed between the upper moving block 320 and the upper connecting block 310, with extending along the third direction, so that the upper moving block 320 moves with respect to the upper connecting block 310.

The upper driver 330 provides a driving force to the upper moving block 320, so as to be moved with respect to the upper connecting block 310, and the driving force from the upper driver 330 is transmitted to the upper moving block 320 or the upper connecting block 310 through the upper transmission 340.

The upper frame 350 is disposed at an outside of the upper moving block 320, and may be used for a frame combining the manipulating unit 200 with an inside of the circular frame 50.

The upper unit 300 further includes a connecting frame 360. A first end of the connecting frame 360 is fixed to both sides of the upper moving block 320, and a second end of the connecting frame 360 is fixed to both sides of the central connecting block 410 of the central unit 400, so that the upper unit 300 and the central unit 400 are connected and fixed with each other.

Here, the connecting frame 360 extends along an inclined direction, and thus, the central unit 400 is positioned much closer to a first direction X than the upper unit 300. The first direction X is substantially perpendicular to the third direction Z.

Accordingly, the upper unit 300 moves along the third direction, and has one degree of freedom.

The central unit 400 includes a central connecting block 410, a first moving block 420, a second moving block 430 and an extending block 440.

The central connecting block 410 has a rectangular block shape, and extends along a surface formed by a second direction Y which is substantially perpendicular to both of the first and third directions X and Z.

Thus, the central connecting block 410 is disposed like an 'L' shape with the upper connecting block 310.

The central connecting block 410 moves with respect to the first moving block 420, along the first direction X. A first guide 411 is disposed between the central connecting block 410 and the first moving block 420, for guiding the relative movement of the central connecting block 410.

Here, the first guide 411 may be disposed at a center of the central connecting block 410. A first sub guide 412 may be additionally formed at both sides of the central connecting block 410, to guide the relative movement of the central connecting block 410 and the first moving block 420.

The first guide 411 and the first sub guide 412 extend along the first direction, and first driver 413 may be disposed on the first sub guide 412 to provide a driving force for the relative movement of the central connecting block 410 and the first moving block 420. Here, the first driver 413 may be disposed adjacent to the first guide 411, but not limited thereto.

The first moving block 420 has a rectangular block shape similar to the central connecting block 410, and extends parallel with a surface formed by the first and second directions X and Y.

The first moving block 420, as explained above, moves along the first direction with respect to the central connecting block 410, and the moves along the second direction with respect to the second moving block 430.

For performing the above movements of the first moving block 420, a second guide 420 extends between the first moving block 420 and the second moving block 430, and a second sub guide 422 may further extend between the first moving block 420 and the second moving block 430.

Here, the second guide 421 is disposed at a center of the first moving block 420, and a second sub guide 422 is additionally formed at both ends of the first moving block 420, to guide the relative movement of the first moving block 420 and the second moving block 430.

The second guide 421 and the second sub guide 422 extend along the second direction, and a second drive (not shown) may be disposed on the second sub guide 420 to provide a driving force for the relative movement of the first moving block 420 and the second moving block 430. Here, the second drive may be disposed adjacent to the second guide 421, but not limited thereto.

The second moving block 430 has a rectangular block shape, and extends parallel with a surface formed by the first and second direction X and Y.

The second moving block 430 moves along the second direction Y with respect to the first moving block 420, and an extending block 440 is fixed to a lower surface of the second moving block 430.

An extending rotating portion 441 is fixed on a lower surface of the extending block 440, and the extending rotating portion 441 rotates with respect to the third direction, and thus, the manipulating part 500 may rotate with respect to the extending block 440.

Accordingly, the central unit 400 moves along the first and second directions, and has two degrees of freedom.

Thus, the upper unit 300 and the central unit 400 are combined with each other, and relatively move along the first to third directions X, Y and Z.

The manipulating par 500 includes a fixing unit 510, a body cover 520, a manipulating frame 530, a body driver 540 and a needle unit 550.

The fixing unit 510 is connected to the extending rotating portion 441 connected to the lower surface of the extending block 440, and rotates with respect to the third direction.

Here, alternatively, the extending rotating portion 441 may be fixed without rotation, and then, the fixing unit 510 may be also fixed without any degree of freedom.

However, the extending rotating portion 441 may rotate with respect to the third direction, and thus, hereinafter, the extending rotating portion 441 is assumed to be rotated.

In addition, the rotation or the fixation of the extending rotating portion 441 may be selected properly.

The fixing unit 510 includes a vertical extending portion 511, a horizontal extending portion 512 and a circular fixing portion 513

A first end of the vertical extending portion 511 is fixed to the extending rotating portion 441, and a pair of vertical extending portions 511 extends along the third direction. A second end of the vertical extending portion 511 is fixed to the horizontal extending portion 510 which extends along the second direction.

Thus, a passing portion is formed at a center where the vertical extending portion 511 and the horizontal extending portion 512 are connected.

The circular fixing portion 513 is disposed at each center of the pair of the vertical extending portions 511, and has a cylindrical shape and is fixed to the vertical extending portions 511.

Thus, when the extending rotating portion 441 rotates with respect to the third direction, the vertical extending portion 511, the horizontal extending portion 512 and the circular fixing portion 513 rotate along the rotating direction of the extending rotating portion 441 at the same time.

The body cover 520 is disposed between the pair of circular fixing portions 513, which is at the passing portion formed by the vertical extending portion 511 and the horizontal extending portion 512, and is fixed by the circular fixing part 513.

Here, the body cover 520 has a cylindrical shape with a hollow shape, and extends along a fourth direction U illustrated in FIG. 6.

The fourth direction U is inclined with the first direction X by a first angle, and may be variously defined according to an extending shape of the body cover 520.

The manipulating frame 530 includes a body 531, an extending portion 532 and a sliding base 533, and rotates with respect to the body cover 520 with a rotating axis of the fourth direction.

The body 531 passes through the body cover 520, and is rotatably combined with the body cover 520. The body driver 540 is fixed to a first end of the body 531.

Here, the body driver 540 may provide a rotating driving force to the body 531, and thus the body 531 may rotate with respect to the body cover 520 with a rotating axis of the fourth direction.

The extending portion 532 extends from a second end of the body 531, and extends inclined with the fourth direction by a predetermined angle.

The sliding base 533 is formed at an end of the extending portion 532, and the sliding base 533 forms a sliding surface having a predetermined area, and the sliding surface extends along a fifth direction V as illustrated in FIG. 6.

Here, the fifth direction V is inclined with the first direction X by a second angle, and the second angle may be different from the first angle.

The needle unit 550 includes a needle base 551, a needle 552 and a needle fixing portion 553, and the needle unit 550 performs the operation at the operation position A.

The needle base 551 has a rectangular block shape, and moves on the sliding base 533 along the fifth direction with respect to the sliding base 533.

The needle 552, as illustrated in the figure, may be a curved needle and performs the operation at the operation position A. The needle fixing portion 553 fixes the needle 552 on the needle base 551.

Accordingly, the manipulating part 500 rotates with respect to the third direction (option), rotates with respect to the fourth direction, and moves along the fifth direction, which means that the manipulating part 500 may have two or three degrees of freedom.

Thus, the manipulating unit 200, entirely, may have five or six degrees of freedom.

Further, the manipulating unit 200 moves along the rotating guide 110, and the operating table 40 moves up and down by the lifting part 16, so that the end of the needle 552 at the robot platform 1 may be positioned with various kinds of degrees of freedom.

Figure 9:
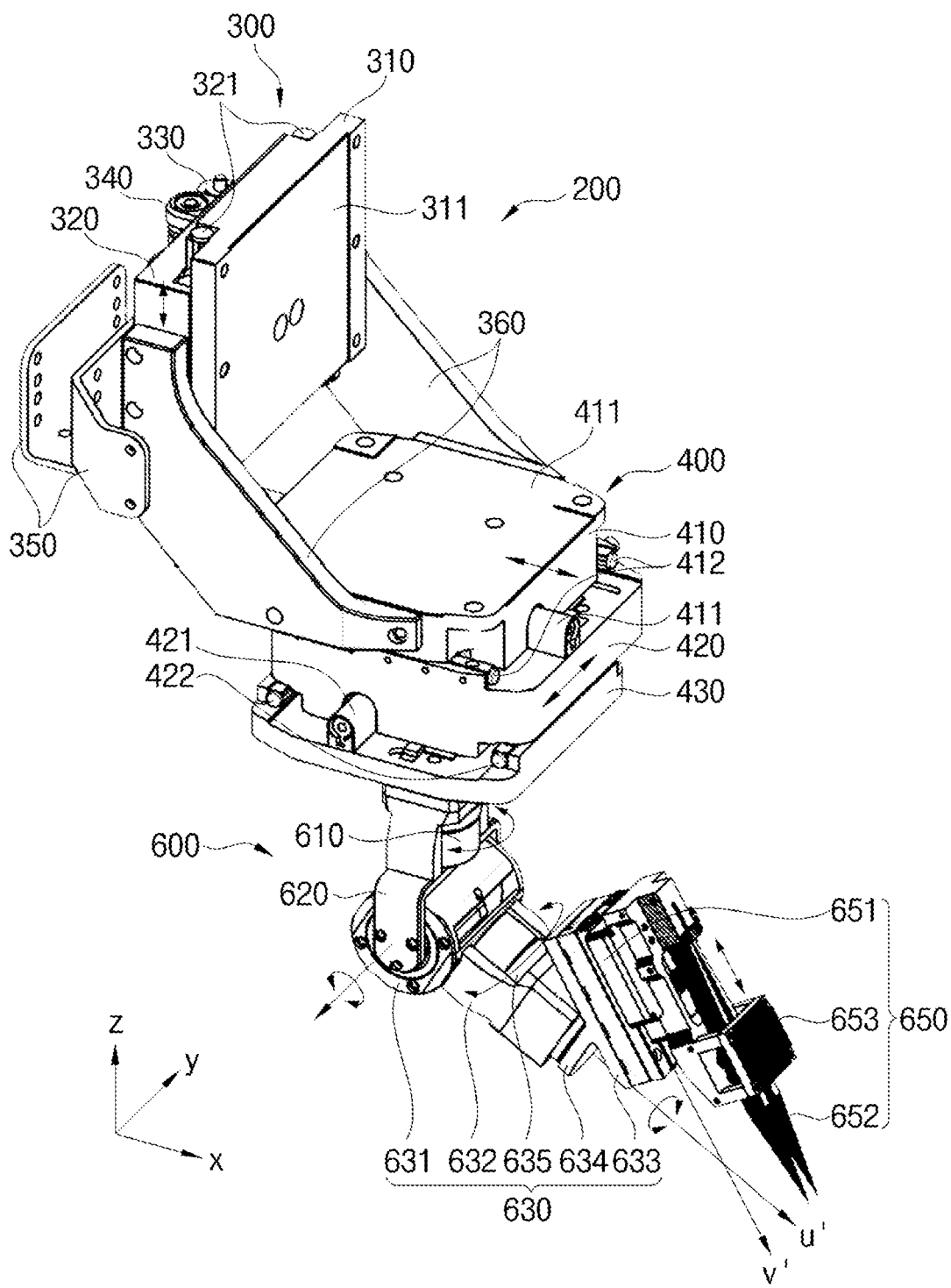
FIG. 9 is a perspective view illustrating a manipulating unit of a robot platform according to another example embodiment of the present invention.
Figure 10:
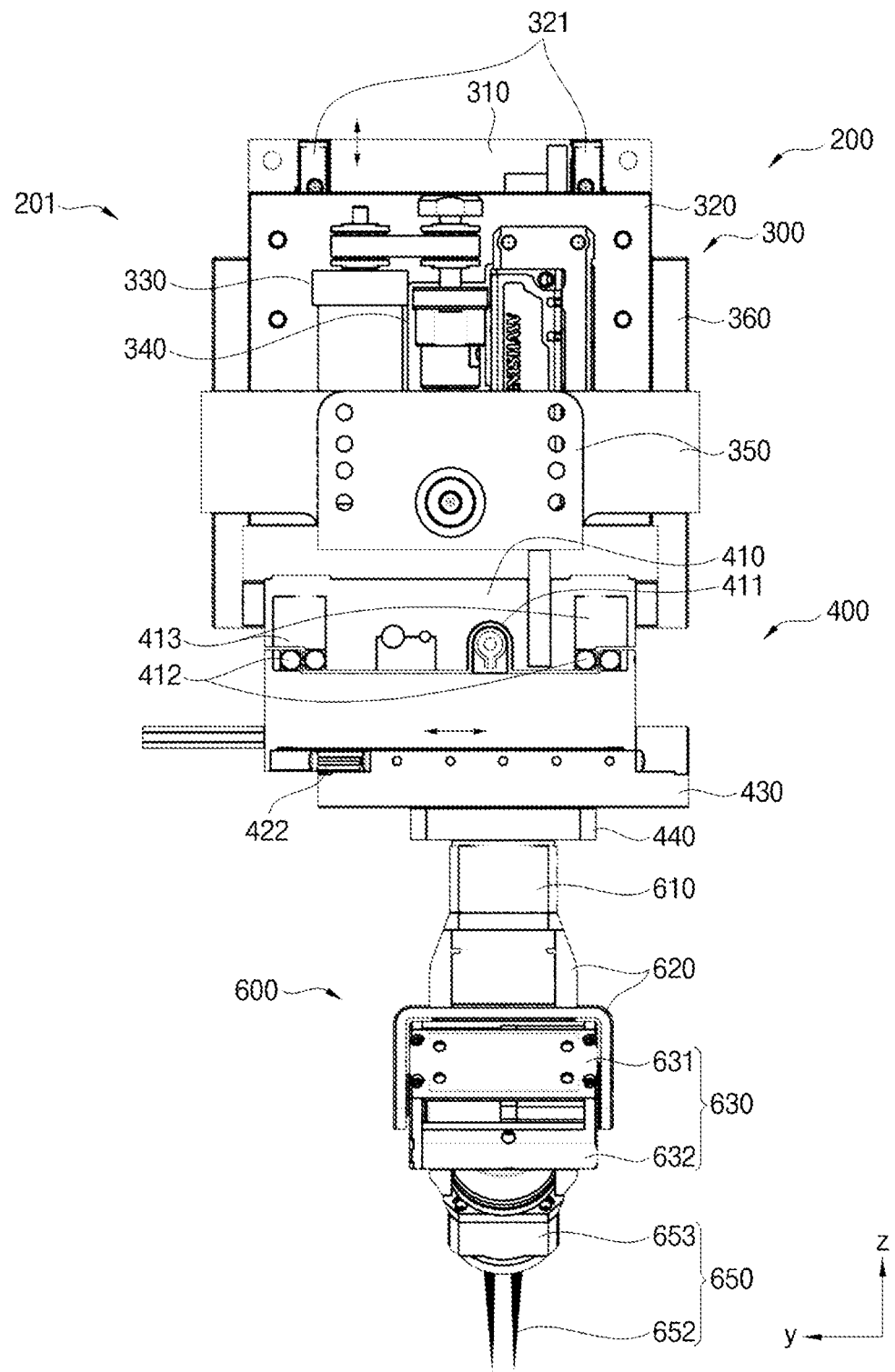
FIG. 10 is a rear view illustrating a manipulating unit of FIG. 9.
Figure 11:
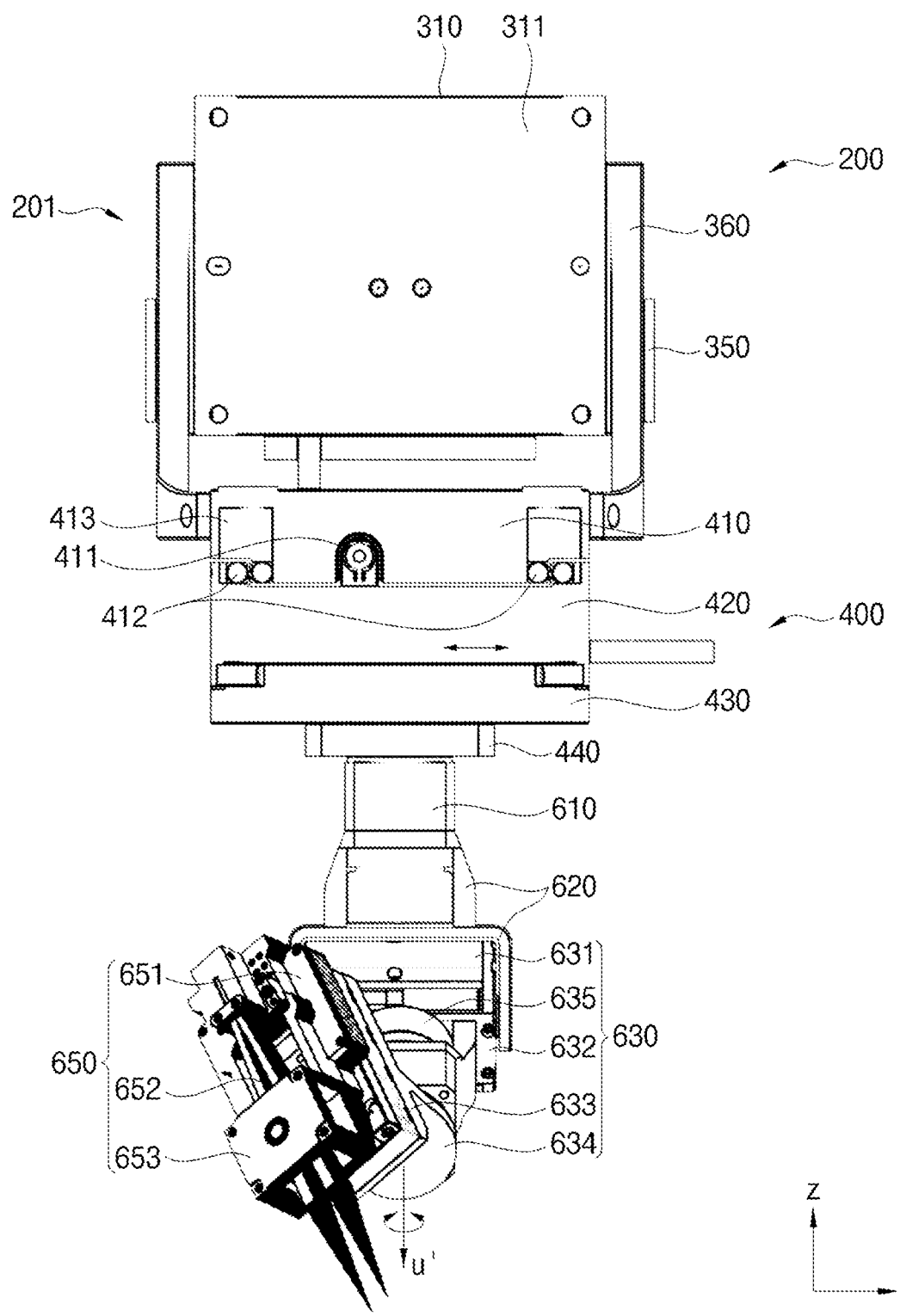
FIG. 11 is a front view illustrating a manipulating unit of FIG. 9.

FIG. 9 is a perspective view illustrating a manipulating unit of a robot platform according to another example embodiment of the present invention. FIG. 10 is a rear view illustrating a manipulating unit of FIG. 9. FIG. 11 is a front view illustrating a manipulating unit of FIG. 9.

The manipulating unit 201 of the robot platform according to the present example embodiment is substantially same as the manipulating part 200 of the robot platform explained referring to FIGS. 1 to 8, except for the manipulating part 600, and omitting the extending block 440 and the extending rotating portion 441, and thus the same reference numerals are used for the same elements and any repetitive explanation will be omitted.

Referring to FIGS. 9 to 11, a manipulating part 600 of the manipulating unit 201 includes a first rotating part 610, a fixing unit 620, a manipulating frame 630 and a needle unit 650.

The first rotating part 610 is directly fixed to a center of a lower surface of a second moving block 430 in the central unit 400, and is rotated with respect to the third direction.

The fixing unit 620 extends along the third direction from the lower surface of the second moving block 430. The first rotating part 610 is fixed to an upper side of the fixing unit 620, and a rotating body 631 of the manipulating frame 630 is fixed to a lower side of the fixing unit 620.

For example, the fixing unit 620 is formed as a pair, and both ends of the fixing unit 620 are fixed to a rotating axis of the rotating body 631, and thus, the rotating body 631 is rotated with respect to the both ends of the fixing unit 620 with a rotating axis of the second direction.

The manipulating frame 630 includes the rotating body 631, an extending portion 632, a sliding base 633, a rotating base 634 and a second rotating part 635.

Here, the rotating body 631 has a cylindrical shape, and as explained above, are fixed to both ends of the fixing unit 620 and is rotated with respect to the second direction.

A pair of the extending portions 632 are extended from a side of the rotating body 631, and the extending direction of the extending portions 632 may be a sixth direction U' as illustrated in FIG. 9.

Here, the sixth direction U' is inclined with the first direction X by a third angle, and may be defined variously based on the connecting position of the rotating body 631.

The extending portion 632 is fixed with the rotating body 631, and rotates with the rotation of the rotating body 631, at the same time.

The second rotating part 635 is connected or combined between the pair of the extending portion 632, and the second rotating part 635 rotates with respect to the sixth direction. Here, the second rotating part 635 may be a cylindrical shape.

In addition, the rotating base 634 is fixed to an end surface of the second rotating part 635, and thus the rotating base 634 rotates with the rotation of the second rotating part 635 at the same time.

The sliding base 633 extends from a side of the rotating base 634. The sliding base 633 forms a sliding surface with a predetermined area, and the sliding surface extends along a seventh direction V' as illustrated in FIG. 9.

Here, the seventh direction V' is inclined with the first direction X by a forth angle, and the forth angle is different from the third angle.

The needle unit 650 includes a needle base 651, a needle 652 and a needle fixing portion 653, and the needle unit 650 performs the operation in the operation position A.

The needle base 651 has a circular block shape, and moves along the seventh direction on the sliding base 633 with respect to the sliding base 633.

The needle 652, in the present example embodiment, may have a straight needle shape as illustrated in the figure, and performs the operation in the operation position A. The needle fixing portion 653 fixes the needle 652 on the needle base 651.

Accordingly, the manipulating part 600 has four degrees of freedom, such as the rotation with respect to the third direction, the rotation with respect to the second direction, the rotation with respect to the sixth direction, and the movement along the seventh direction.

Thus, the manipulating unit 201 may have seven degrees of freedom, in total.

Further, the manipulating unit 201 moves along the rotating guide 110, and the operating table 40 moves up and down by the lifting part 16, so that the end of the needle 552 of the robot platform 1 may be positioned with more increased degrees of freedom.

According to the present example embodiments, an operation on a fine nerve interface like a peripheral nerve manipulation may be performed more accurately, precisely and finely. The robotic platform may have a relatively simple structure and perform all kinds of driving, and thus the operation may be performed with various kinds of positions and postures.

The robotic platform has many degrees of freedom, and thus fine, accurate, precise and complex operation may be performed, and a plurality of manipulating units may be positioned at various kinds of positions on a rotating guide and thus the operation may be performed more efficiently.

Here, an upper unit and a central unit move in a horizontal direction along first to third directions, and a manipulating part rotates or slides along two axes inclined with respect to the first direction additionally, and thus a needle may perform the operation with various kinds of positions and postures.

In addition, the needle performing the operation accesses to an object with sliding, and thus the operation may be performed more accurately and precisely. Various kinds of needles may be selected, and various kinds of operations may be performed.

In addition, the operation may be recorded and monitored through a central opening portion, and the feed-back control for preventing the position or the posture of the manipulating units from interfering in the operation may be performed.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:
1. A robot platform comprising:
a manipulator performing an operation over an operating table; and
a recorder recording the operation through the manipulator,
wherein the manipulator comprises:
a rotating guide having an opening portion through which the recorder records, and having a guide rail at a side;
a plurality of rotating movers combined with the rotating guide and moving along the guide rail; and
a plurality of manipulating units respectively fixed to the rotating movers, a manipulating part performing the operation being connected to an end of each of the manipulating units.

2. The robot platform of claim 1, wherein the rotating guide has a circular plate shape, and the rotating movers rotates with respect to a center of the rotating guide along the guide rail.

3. The robot platform of claim 2, wherein each of the rotating movers comprises:
an upper block disposed at an upper side of the rotating guide and partially facing an upper side of the rotating guide;
a lower block disposed at a lower side of the rotating guide and partially facing a lower side of the rotating guide; and
a central block connecting the upper block with the lower block, and moving along the guide rail, the manipulating unit being fixed to a rear side of the central block.

4. The robot platform of claim 1, wherein each of the manipulating units further comprises an upper unit fixed to the rotating mover, and a central unit connected to the upper unit, the manipulating unit being connected to a lower side of the central unit,
wherein each of the upper unit and the central unit has three degrees of freedom, capable of moving along a first direction X, a second direction Y and a third direction Z substantially perpendicular to one another.

5. The robot platform of claim 4, wherein the upper unit comprises:
an upper connecting block fixed to the rotating mover;
an upper moving block moving along the third direction with respect to the upper connecting block at a rear side of the upper connecting block; and
a connecting frame connecting the upper moving block with the central unit.

6. The robot platform of claim 5, wherein the upper unit is disposed at an outside of the rotating guide, and the connecting frame extends from the outside of the rotating guide to a lower portion of the rotating guide along an inclined direction so that the central unit and the manipulating unit are disposed at an inside lower portion of the rotating guide.

7. The robot platform of claim 4, wherein the central unit comprises:
a central connecting block connected to the upper unit and moving along the first direction with the upper unit;
a first moving block connected to a lower portion of the central connecting block; and
a second moving block moving along the second direction with respect to the first moving block at a lower portion of the first moving block.

8. The robot platform of claim 4, wherein the manipulating part comprises:
a fixing unit rotating with respect to the central unit with a rotating axis of the third direction;
a manipulating frame rotating with respect to the fixing unit with a rotating axis of a fourth direction U; and a needle unit moving along a fifth direction V with respect to the manipulating frame.

9. The robot platform of claim 8, wherein the fourth direction is inclined with respect to the first direction by a first angle, and the fifth direction is inclined with respect to the first direction by a second angle different from the first angle.

10. The robot platform of claim 8, wherein the fixing unit comprises:
   a pair of vertical extending portions extending along the third direction from an extending rotating portion of the central unit, the extending rotating portion rotating with respect to the third direction;
   a horizontal extending portion connecting ends of the pair of vertical extending portions with each other; and
   a pair of circular fixing portions fixed to a center of each of the pair of vertical extending portions, the manipulating frame passing between the pair of circular fixing portions.

11. The robot platform of claim 8, wherein the manipulating portion further comprises a body cover passing through and fixing the fixing unit along the fourth direction, wherein the manipulating frame comprises:
   a body portion passing through the body cover, and rotating with respect to the body cover with a rotating axis of the fourth direction;
   an extending portion extending from the body portion; and
   a sliding base forming a sliding surface along the fifth direction at an end of the extending portion.

12. The robot platform of claim 8, wherein the needle unit comprises:
   a needle base sliding along the fifth direction with respect to the manipulating frame;
   a needle disposed on the needle base; and
   a needle fixing portion fixing the needle.

13. The robot platform of claim 4, wherein the manipulating part comprises:
   a first rotating part rotating with respect to the central unit with a rotating axis of the third direction;
   a fixing unit covering the first rotating part and extending along the third direction;
   a manipulating frame combined with the fixing unit and rotating with respect to the second direction and a sixth direction U'; and
   a needle unit moving along a seventh direction V' with respect to the manipulating frame.

14. The robot platform of claim 13, wherein the sixth direction is inclined with respect to the first direction by a third angle, and the seventh direction is inclined with respect to the first direction by a fourth angle different from the third angle.

15. The robot platform of claim 13, wherein the manipulating frame comprises:
   a rotating body combined with an end of the fixing unit and rotating with respect to the second direction;
   an extending portion extending along the sixth direction from the rotating body; and
   a second rotating portion combined with the extending portion and rotating with respect to the sixth direction.

16. The robot platform of claim 15, wherein the manipulating frame further comprises:
   a rotating base fixed to an end surface of the second rotating portion; and
   a sliding base forming a sliding surface from an end of the rotating base to the seventh direction.

17. The robot platform of claim 13, wherein the needle unit comprises:
   a needle base sliding along the seventh direction with respect to the manipulating frame;
   a needle disposed on the needle base; and
   a needle fixing portion fixing the needle.

* * * * *